(12) United States Patent
Zhang et al.

(10) Patent No.: US 8,241,301 B2
(45) Date of Patent: Aug. 14, 2012

(54) GUIDED PUNCTURING NEEDLE AND PUNCTURING GUIDING METHOD

(75) Inventors: Hui-Lin Zhang, Beijing (CN); Su Feng, Beijing (CN); Wei-Jian Feng, Beijing (CN)

(73) Assignees: Huilin Zhang, Beijing (CN); Su Feng, Beijing (CN); Zhejiang Kindly Medical Devices Co., Ltd., Zhejiang (CN)

( * ) Notice: Subject to any disclaimer, the term of this patent is extended or adjusted under 35 U.S.C. 154(b) by 1011 days.

(21) Appl. No.: 12/161,729

(22) PCT Filed: Jan. 23, 2007

(86) PCT No.: PCT/CN2007/000254
§ 371 (c)(1),
(2), (4) Date: Jul. 22, 2008

(87) PCT Pub. No.: WO2007/082494
PCT Pub. Date: Jul. 26, 2007

(65) Prior Publication Data
US 2010/0280354 A1    Nov. 4, 2010

(30) Foreign Application Priority Data
Jan. 23, 2006   (CN) .......................... 2006 1 0001830

(51) Int. Cl.
*A61B 19/00*    (2006.01)

(52) U.S. Cl. ........................................ 606/130; 600/407
(58) Field of Classification Search .................. 600/407, 600/411, 417, 427, 461; 604/116, 117; 606/130, 606/185
See application file for complete search history.

(56) References Cited

U.S. PATENT DOCUMENTS

| | | | | |
|---|---|---|---|---|
| 5,575,798 A * | 11/1996 | Koutrouvelis | ................ | 606/130 |
| 6,030,348 A * | 2/2000 | Unger et al. | ................... | 600/564 |
| 6,334,067 B1 * | 12/2001 | Brabrand | ...................... | 600/427 |
| 6,949,105 B2 * | 9/2005 | Bryan et al. | .................. | 606/130 |

\* cited by examiner

*Primary Examiner* — Francis Jaworski

(57) ABSTRACT

A guide puncturing needle which is integratively used with a scanning and detecting device, such as CT, MRI or the like, and provides puncturing, biopsy, injection, implanting, and the physical diagnose and therapy, such as RF, microwave, freezing, laser and the like, and a puncturing guide method for applying the puncturing needle to puncture are provided. Since the guide puncturing needle is provided with a needle-entering angle guide means (2), a puncturing layer levelling component (31), a needle-entering reference line levelling component (32), whether the CT gantry and the MRI scanning layer are at any angle, the actual needle-entering layer is always adjusted to just superpose to the CT scanning layer, the actual needle-entering angle is always just the same as the needle-entering angle needed for the scanning and detecting device, thus allow the puncturing needle to arrive at the focus point exactly accurately.

5 Claims, 12 Drawing Sheets

GUIDED PUNCTURING NEEDLE AND PUNCTURING GUIDING METHOD

BACKGROUND OF THE INVENTION (a) Field of the Invention

The present invention is related to a medical instrument, more particularly to a guided puncturing needle and puncturing method being integrally used with scanning and detecting devices such as CT or MRI or the like to provide puncturing, biopsy, injection, implanting and the physical diagnose and therapy such as RF, microwave, freezing, laser and the like inside the scanning layer.

(b) Description of the Prior Art

In case of pathological changes happen inside human body, focus point biopsy or therapy are sometimes performed by using puncturing, wherein focus point positioning relative to skin and needle-entering depth are normally relied on instruments (such as scanning devices of CT or MRI, etc.) which usually include that: the position of focus point on cross-section of human body is first detected by CT scanning device; next, the best needle-entering position and angle on skin surface of the layer is selected and the precise positions of focus point and needle-puncturing are decided according to the 3D image of the needle-entering layer, needle-entering angle and needle-entering depth. Although CT scanning device can precisely pinpoint the 3D needle-entering angle and depth, the puncturing process is performed after the patient being removed away from scanning layers of CT. Under present technological conditions, the doctor has to rely on his/her own judgment to determine the approximate direction for needle-entering after patent left the CT scanning device to perform puncturing, then CT scanning is performed again for confirmation. As there are more human factors usually causing needle-entering inaccuracies, therapy precision is therefore affected. Sometimes repetitive needle-entering may be required and puncturing through by mistake may happen in serious occasions causing great pain and risks on the patient. In view of this, puncturing positioning devices have been developed by people in the business, including that:

U.S. Pat. No. 5,957,933 discloses a 3D guiding device being combined with CT scanning device for guiding puncturing needle to enter patient's body. The 3D guiding device being able to puncturing needle guiding device to precisely reach the focus point from different directions of human body and to display the whole needle-entering process comprises complicated mechanical structure and control system with expensive manufacturing cost and is inconvenient for operation.

U.S. Pat. No. 5,196,019 discloses a puncturing needle positioning instrument which does not require complicated equipment and has a much simpler structure than the 3D guiding device disclosed by U.S. Pat. No. 5,957,933 to be handled by the single hand of a single person. The main body of the device as shown in FIG. 1 comprises a pairs of rings, i.e. outer ring 30' and inner ring 40'; the bow shaped circle of outer ring 30' is marked with angle graduations; the inner ring 40' being rotably made inside outer ring 30' and being aligned with outer ring 30' on the same axis is installed with a puncturing needle guiding device. The outer ring 30' is made with saw-teeth on the bow shaped inner curvilinear surface thereof, while inner ring 40' is made with an elastic thrust claw for engaging and detaching with the saw-teeth; the puncturing needle guiding device is made with a handle 50' on the plane surface thereof for locking the elastic thrust claw into the saw-teeth by rotating the handle when the puncturing needle guiding device is moved to the puncturing position. Although the device of simple structure can be held by hand for use, the calibrating component for ensuring complete superposition of actual needle-entering layer and scanning layer of focus point as well as ensuring that actual needle-entering angle is completely identical to the CT requested needle-entering angle is not installed, hence said CT guided puncturing needle positioning instrument is only suitable for use when CT gantry is perpendicular to the hospital bed at zero degree without precision. As focus point scanning layer cannot be obtained unless the CT gantry is declined to a certain angle, the doctor is unable to adjust the angle of needle-entering layer using this guiding instrument, hence, and the doctor can only made the adjustments by visual judgment and experience. Besides, as the device is a guiding instrument independent to the puncturing needle, puncturing through by mistake may happen in serious occasions that causes great inconvenience to doctor's therapy as well as great pains and risks to the patient.

In view of the inconveniences, unprecise positioning problems and separation of the puncturing needle and guiding instrument in present arts, the application for patent is therefore submitted.

SUMMARY OF THE INVENTION

Aiming to solve the above described technical problems, the present invention is purposed to disclose a puncturing needle guiding device having accurate positioning, simple structure but compact, and convenience in operation.

The second purpose of the present invention is to disclose a method for guiding the puncturing needle to enter human body with the scanning and detecting device being inclined at random angle to hit the focus point, wherein after the patient is scanned by the scanning device such as CT and the like for confirming the needle-entering angle and needle-entering layer and horizontally moved away from the CT scanning layer, the said method allows the puncturing needle to be precisely accurately guided to the focus point by utilizing the needle-entering angle guide means, puncturing layer leveling component and reference line leveling component of the guiding component of the puncturing needle guiding device according to the inclined angle of and the needle-entering angle and needle-entering depth provided by the scanning and detecting equipment from different direction of human body sectional scanning layers.

To achieve aforesaid purposes, the present invention discloses a puncturing needle guiding device which includes: puncturing needle and guiding device for fixing and indicating needle-entering angle of puncturing needle, wherein said guiding device comprises:

A needle-entering angle guide means, wherein said puncturing needle is rotably connected with guide means via a connecting mechanism; said guide means is made with a needle-entering angle reference line and an angle indicating device for indicating the intersected angle between actual needle-entering direction of the puncturing needle and the reference line;

A puncturing layer leveling component having an angle indicating device for indicating the deviatingly rotated angle of the puncturing needle rotating plane; said guide means is sidely affixed to the puncturing layer leveling component, and the deviating angle rotating axis of the angle indicating device of said puncturing layer leveling component for indicating the deviatingly rotated angle of the puncturing needle rotating plane is parallel to said guide means.

A needle-entering reference line leveling component to adjust the needle-entering angle reference line on the guide means to be on the same plane of the hammer weight line, wherein said needle-entering reference line leveling component is made with an angle indicating device having its deviatingly rotated axis being perpendicular to the deviating angle rotating axis of the angle indicating device on said puncturing layer leveling component;

Said guiding device is further made with a leveling benchmark for instructing the horizontal line on rotating puncturing plane to be parallel to the needle-entering layer.

The angle indicating devices for said guide means, puncturing plane leveling component, reference line leveling component are digit type angle indicator, or mechanical type angle indicator marked with angle scales and pointer, or bubble type level gauge.

The angle indicating device of said guide means is preferably an angle indicating device of mechanical type flat plate angle indicator with angle scale; rotating center of said puncturing needle being used as the pointer for the angle indicator is superposed with the angle measuring center of the flat plate angle indicator, the rotating plane of puncturing needle is parallel to the plate surface of said flat plate angle indicator, and said puncturing angle reference line being passing through the rotating center of said puncturing needle is on the plate surface of said flat plate angle indicator.

The angle indicating device of said puncturing layer leveling component is preferably a mechanical type angle indicator, said mechanical type angle indicator is a hammer weight type swing pointer angle indicator comprising angle indicating plate and hammer weight swing pointer being concentrically installed with the circle of angle indicating plate; the swing plane of the hammer weight swing pointer of said puncturing layer leveling component is perpendicular to the plate surface of flat plate angle indicator of said guide means; and the swing plane of the hammer weight swing pointer of said puncturing layer leveling component is perpendicular to the swing plane of the hammer weight swing pointer angle indicator of the reference line leveling component.

Said flat plate angle indicator for needle-entering angle indication is centrally made with a center hole or locking rail being connected with puncturing needle, said puncturing needle is affixed to said needle-entering angle indicating device via the needle holder.

Said scanning layer leveling benchmark is connected to the plate surface of flat plate angle indicator via a column to form the T shaped protruding frame, and the axis of the leveling benchmark is located on the rotating plane of puncturing needle. The number of T shaped protruding frame is 1-2.

Said guiding device is made with a top open rectangular casing, said guide means of needle-entering angle indicator is sidely affixed to said rectangular casing, said puncturing layer leveling component and reference line leveling component are installed inside the casing, the angle indicating devices of said puncturing layer leveling component and reference line leveling component are exposed via the top opening; and said casing opening is lockingly covered by a transparent cover.

The puncturing layer leveling component and reference line leveling component of said guide means are mutually fixed; a rotating spindle is at the same axis with the angle rotating axis of puncturing layer leveling component; said puncturing layer leveling component and reference line leveling component being integrally fixed is pivotally installed on said casing with rotating spindle as the pivotal axis; and said rotating spindle is protrudingly extended out of casing, wherein the external surface being installed with protrudingly extended rotating spindle is made with rotating angle scale for the rotating spindle, and a knob with pointer is affixed to the said protrudingly extended rotating spindle.

Said guiding device is made with a L type right angle bended plate comprising two flat plates, said needle-entering angle guide means and said reference line leveling component are installed on one of the flat plate on the L type right angle bending plate, and angle swing planes of said needle-entering guiding means and said reference line leveling component are parallel to the surface of said flat plate; said puncturing layer leveling component is installed on another flat plate of the L type right angle bending plate, and the angle swing plane of said puncturing layer leveling component is parallel to the surface of another flat plate.

The angle scale of said flat plate needle-entering angle indicator is 0-360°, preferably 0-180°, or 0-90°.

The present invention also discloses a puncturing guiding method being applied on the above said puncturing needle guiding device, wherein it includes the following steps:
1) The 3D coordinates of the focus point position is detected by CT or MRI scanning device to confirm the puncturing sectional layer Y0Z, and the skin needle-entering point L and projection line of scanning layer on the body surface; wherein the needle-entering angle and depth is calculated by the angle of the line connecting the puncturing hitting focus point and skin needle-entrance point relative to horizontal line, or vertical line of horizontal line and the length of the line;
2) The puncturing needle is installed on the needle-entering angle indicating plate of the guide means;
3) Leveling the puncturing needle-entering angle: the needle-entering angle of the puncturing needle is adjusted on the angle scale plate of guide means along the puncturing needle axis to corresponding angle according to the needle-entering angle confirmed by CT or MRI scanning device;
4) The needle point of puncturing needle is aimed at the skin needle-entering point confirmed by the scanning and detecting equipment, thereby allowing the needle-entering angle hammer weight of reference leveling component is pointed to the 0° line of the angle indicating base plate, or the pointer of hammer weight is pointed to 0 scale;
5) The puncturing needle guiding device is deviatingly rotated according to the inclined angle of CT gantry or the deviatingly rotating angle of MRI scanning device until reaching the same angle as the inclined angle $\alpha$ of CT gantry or MRI scanning device displayed by the angle display device of scanning layer leveling component;
6) The scanning layer leveling benchmark is aimed at the axis of puncturing needle and the projection line of scanning layer on body surface; and
7) The needle is punctured into the human body till the needle-entering depth confirmed by CT or MRI scanning devices so as to hit the focus point.

If the reference line leveling component is a bubble type level gauge in step 4), the bubble of the bubble type level gauge shall be positioned at the center.

The result is confirmed by CT scanning after the puncturing is performed.

As summarized from the above descriptions, the present invention is through installations of the puncturing layer and needle-entering layer leveling components and needle-entering angle guide means to allow that no matter if the CT gantry is perpendicular to plane X0Y, i.e. perpendicular to the lying detected human body, or if it is inclined at an angle $\alpha$ relative to human body, as long as the puncturing needle is inclined at the same angle based on reference line as the standard to perform puncturing according to needle-entering position, needle-entering angle and needle-entering depth detected by CT scanner, the puncturing layer B can be always ensured to completely superpose with CT scanning layer A and hit the focus point accurately. Optimization of the structural relationships between the guide means, needle-entering leveling component, and puncturing layer leveling component, etc. makes the said guiding device very convenient for use, wherein it can be hand held for operation by single person, and the operator is not exposed to radiation (no exposure), so that the operating time is greatly reduced, and the work can be done within 15 minutes.

The puncturing needle guiding device can also adopt mechanical structures to replace the hand held structure, such as the mechanical arm, auxiliary bracing or guide rail supports for the puncturing needle guiding device.

The present invention is detailingly described by the accompanied figures and specific embodiments in the following sections.

DETAIL DESCRIPTION OF THE PREFERRED EMBODIMENTS

The present invention is related to a medical instrument, more particularly to a guided puncturing needle being integrally used with scanning and detecting devices such as CT or MRI or the like to provide puncturing, pathological biopsy, medicine injection, catheter indwelling, bone opening, and implanting solid medicine, chemotherapy or radiotherapy seeds as well as the physical diagnose and therapy such as microwave, RF, freezing, laser and the like inside the scanning layer. As the puncturing needle guiding device is installed with puncturing layer and needle-entering reference leveling components, the actual needle-entering layer of the puncturing needle is always adjusted to completely superpose with scanning layer no matter what angle of the CT gantry is at; further, the actual needle-entering angle is always just the same as the CT requested needle-entering so as to greatly enhance the needle-entering accuracy.

Figure 1:
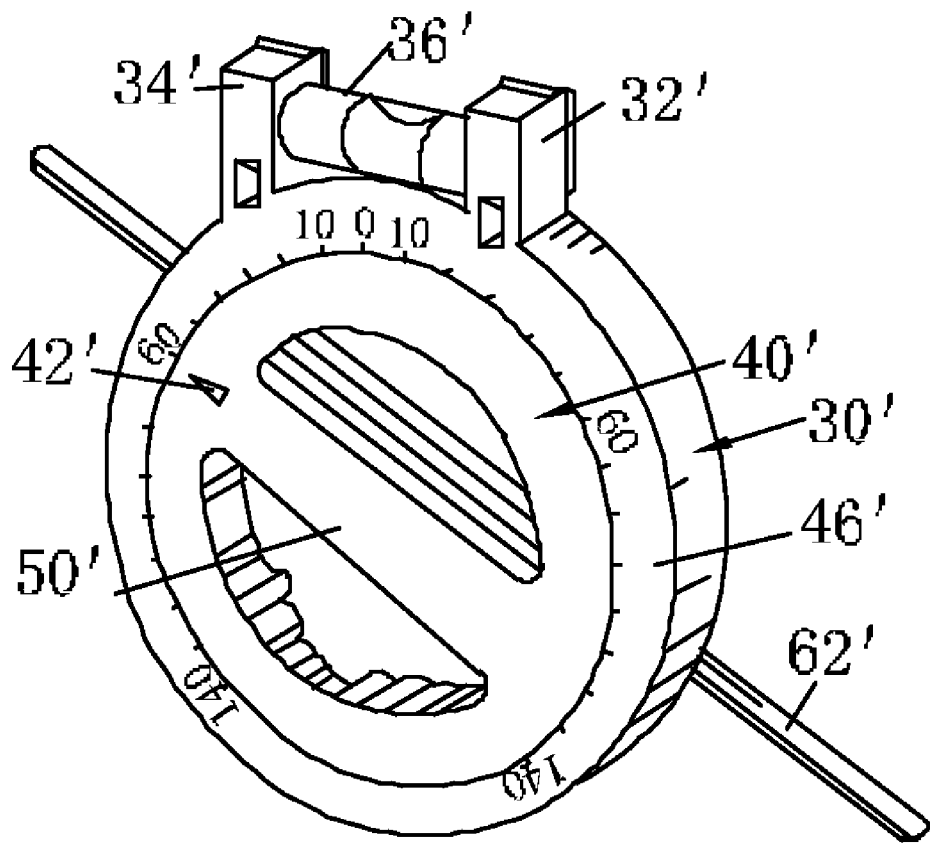
FIG. 1 is a structural schematic view of the existing art U.S. Pat. No. 5,196,019.
Figure 2:
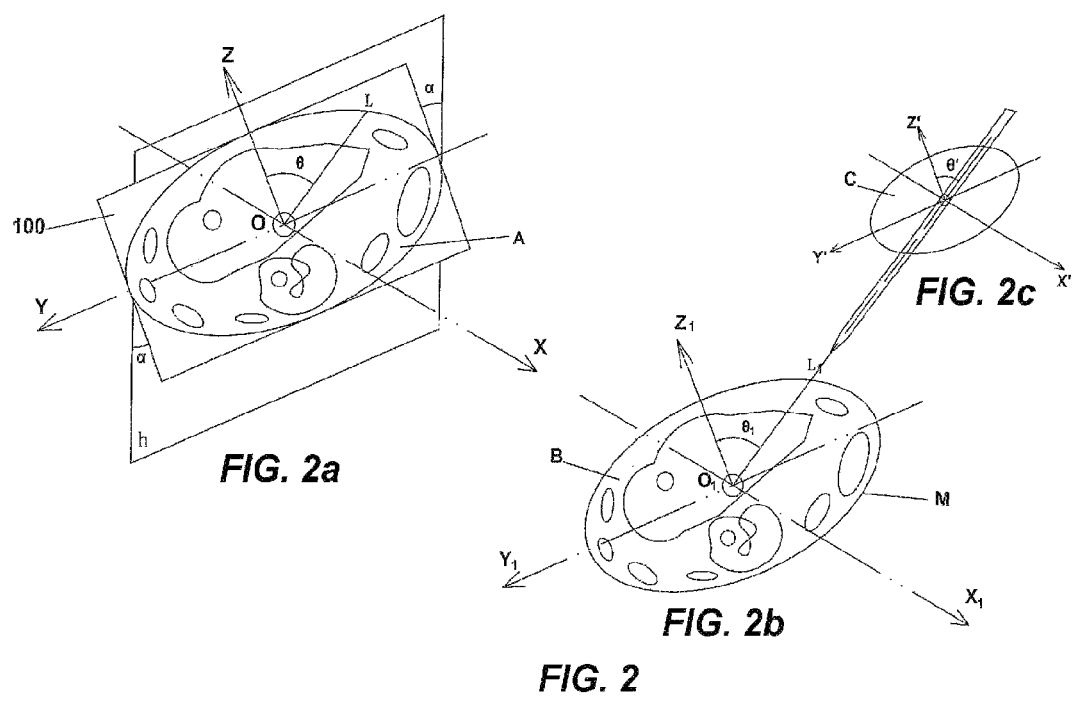
FIG. 2 is the working principle diagram of the present invention.

For the convenience of understanding the present invention, the working principle of the present invention is first described in the following:

As shown in FIG. 2a, A is the scanning layer of focus point with CT scanning and detecting device gantry 100 being inclined at angle α, the scanning layer is generally detected with the human body being lain down flatly, usually the plane of human body is parallel to the horizontal plane, wherein:

Point 0 is the focus point, then the 3D coordinates XYZ0 are established using point 0 as the origin; the axis passing point 0 being parallel to the longitudinal axis of human body is defined as the X axis; the axis on the scanning layer surface A being perpendicular to X axis is defined as Y axis; the axis passing point 0 being located on the same scanning layer of Y axis and being perpendicular to Y axis is defined as Z axis. At the moment, the scanning layer of focus point is Y0Z plane, wherein point L is the puncturing point on the skin, and L0 is the puncturing route whose distance is needle-entering depth; the intersected angle between line L0 and axis Z is the needle-entering angle denoted as θ; the scanner gantry is usually forwardly or backwardly inclined along the Y axis, if the plane passing Y axis being perpendicular to horizontal floor is h, then the intersected angle between the said plane Y0Z and plane h is the inclined angle of CT gantry, and is denoted as α. When α is smaller than 0, CT is backwardly inclined; when α is larger than 0, CT is forwardly inclined; when α equals 0, CT gantry is perpendicular to horizontal floor, i.e. perpendicular to the detected human body that we call zero degree. However, as long as the scanner gantry is rotated along the Y axis for forward or backward inclination at any α angle, the Z axis being as the needle-entering reference line is always perpendicular to Y axis; i.e. the tracking plane formed by the Z axis of needle-entering reference line being inclined forwardly and backwardly along the Y axis is perpendicular to Y axis.

After needle-entering position and needle-entering angle as well as needle-entering depth are confirmed by CT or the like, said needle-entering point is marked at the corresponding position on human body surface, i.e. the skin puncturing point L as well as the intersected line M of YZ plane and the human body; then the doctor punctures needle on the patient according to the detected puncturing point L, intersected line M, needle-entering angle θ, and needle-entering dept OL. Referring to FIG. 2b, assuming $0_1$ is the hitting point of puncturing needle (focus point), and B is the human body cross-section plane on needle-entering layer of the puncturing needle, wherein $0_1$ is the origin of the 3D coordinate system $X_1Y_1Z_10_1$; the axis passing point $0_1$ being parallel to the longitudinal axis of human body is defined as $X_1$ axis; the axis passing point $0_1$ being located on plane B being perpendicular to $X_1$ axis is defined as $Y_1$ axis; the axis passing point $0_1$ being located on plane B as the same as $Y_1$ axis and being perpendicular to $Y_1$ axis is defined as $Z_1$ axis; at this moment, plane $Y_10_1Z_1$ is the needle-entering layer of puncturing needle, and plane B is the sectional image of human body on plane $Y_10_1Z_1$.

As CT detection and operation is done with human body lying on (face up) the inspection bed, the X axis in XYZ0 coordinate system and $X_1$ axis in $X_1Y_1Z_10_1$ coordinate system are the same axis.

Hence, for actual needle-entering hitting point to completely superpose with the focus point, the following two conditions shall be satisfied:

1. The needle-entering plane $Y_1 0_1 Z_1$ of puncturing needle is completely superposed with scanning layer Y0Z of focus point.
2. The reference of needle-entering angle θ shall be just the same, i.e. $0_1 Z_1$ and 0Z are completely superposed to each other.

Only if above said conditions are satisfied, when the doctor punctures the needle according to CT detected needle-entering point, needle-entering angle and needle-entering depth, the actual needle-entering layer and CT scanning layer can be completely superposed and the needle-entering angle can be just the same as the CT requested needle-entering angle. The present invention is therefore based on this principle by utilizing leveling components having puncturing layer and needle-entering references to always ably ensure that no matter how the scanning layer is obtained at any CT gantry situations, the needle-entering layer of the puncturing needle is completely superposed with the scanning layer of focus point as well as that the needle-entering angle is just the same as CT requested needle-entering angle thereby allowing the puncturing needle to arrive at the focus point precisely.

In order to obtain the more appropriate needle-entering point, the CT gantry is often forwardly or backwardly inclined at certain degree along the Y axis. When the gantry is rotated to an angle α, the scanning layer Y0Z is also rotated to an angle α; at the moment, the needle-entering layer $Y_1 0_1 Z_1$ of puncturing needle shall be also rotated to an angle α in the same direction.

In actual needle puncturing operation as shown in FIG. 2c, wherein the puncturing needle is usually fixed on the plane of guide component. Said puncturing needle in rotated on plane C alone the puncturing needle axis piecing through the plane being parallel to plane C and follow the radial guidance on plane C to enter the human body. For easy descriptions and compliance with practical requirements, a coordinate system X', Y', Z', 0' is established on the guide component allowing the coordinate origin 0' to be superposed with center of puncturing needle rotation on plane C, wherein said X' axis is perpendicular to plane C, and Y' and Z' are on plane C.

How to adjust the guide component in order to satisfy the above said two conditions? The plane Y' 0' Z' on guide component and needle-entering plane $Y_1 0_1 Z_1$ shall be on the same plane; first, plane Y' 0' Z' is made parallel to needle-entering plane $Y_1 0_1 Z_1$, wherein the specific method is to install a straight benchmark parallel to Y' axis on the guide component, projection of straight benchmark on patient's body is made parallel to the intersected line M of puncturing layer and human body to allow Y' axis to be parallel to Y axis; then the plane Y'0'Z' is rotated by a angle via the puncturing layer leveling component on guide component according to the inclined angle α of scanner gantry so as to allow plane Y'0'Z' to be parallel to plane $Y_1 0_1 Z_1$; after that, a line on plane Y'0'Z' is made to intersect with and place on the plane $Y_1 0_1 Z_1$; specifically, the guide component is parallel translated allowing puncturing needle to coincide with the puncturing point L, i.e. making plane Y'0'Z' and the needle-entering plane $Y_1 0_1 Z_1$ on the same plane. At this moment, Z' axis and $Z_1$ axis do not necessarily have to be parallel, the Z' axis is adjusted via reference line leveling component to be on the plane perpendicular to the horizontal plane, then the needle-entering angle θ is adjusted to allow θ' to equal to $θ_1$.

In other words, to ensure that actual needle-entering layer is completely superposed with CT scanning layer and actual needle-entering angle θ' is just the same as the CT requested needle-entering angle θ, the following issues must be guaranteed:

1. The plane C of puncturing needle shall be placed at the position allowing its rotating axis X' to be parallel to the X axis of human body longitudinal direction, and make plane Y'0'X' parallel to the plane Y0X; further, since human body is lain on the inspection bed, the plane Y'0'X' being parallel to plane Y0X also means that the plane Y'0'X' is parallel to the horizontal floor no matters how CT scanning is operated, and only that needle-entering reference line 0'Z' can be completely parallel to CT needle-entering reference line. However, who shall do the judgment? A needle-entering reference line leveling device is required to allow that not only the scanning and detection can be done, parallel of 0'Z' and 0Z can also be ensured via the needle-entering reference line rotating axis, and therefore, this needle-entering reference line rotating axis must be parallel to X' axis.
2. The plane C and plane Y0Z must be in parallel. In other words, when CT scanning layer Y0Z is rotated by angle α along Y axis, the plane C shall also rotated by angle α along Y' axis. Therefore, a puncturing layer leveling device is required to ensure plane C being rotated along Y' axis. We call Y' axis as the puncturing layer leveling rotating axis herein.

Only if above said conditions are satisfied, when the doctor punctures the needle according to CT detected needle-entering point, needle-entering angle and needle-entering depth, the actual needle-entering layer and CT scanning layer can be completely superposed and the needle-entering angle can be just the same as the CT requested needle-entering angle. The present invention is therefore based on this principle by utilizing leveling components having puncturing layer and needle-entering references to always ably ensure that no matter how the scanning layer is obtained at any CT gantry situations, the needle-entering layer of the puncturing needle is completely superposed with the scanning layer of focus point as well as that the needle-entering angle is just the same as CT requested needle-entering angle thereby allowing the puncturing needle to arrive at the focus point precisely.

Figure 3:
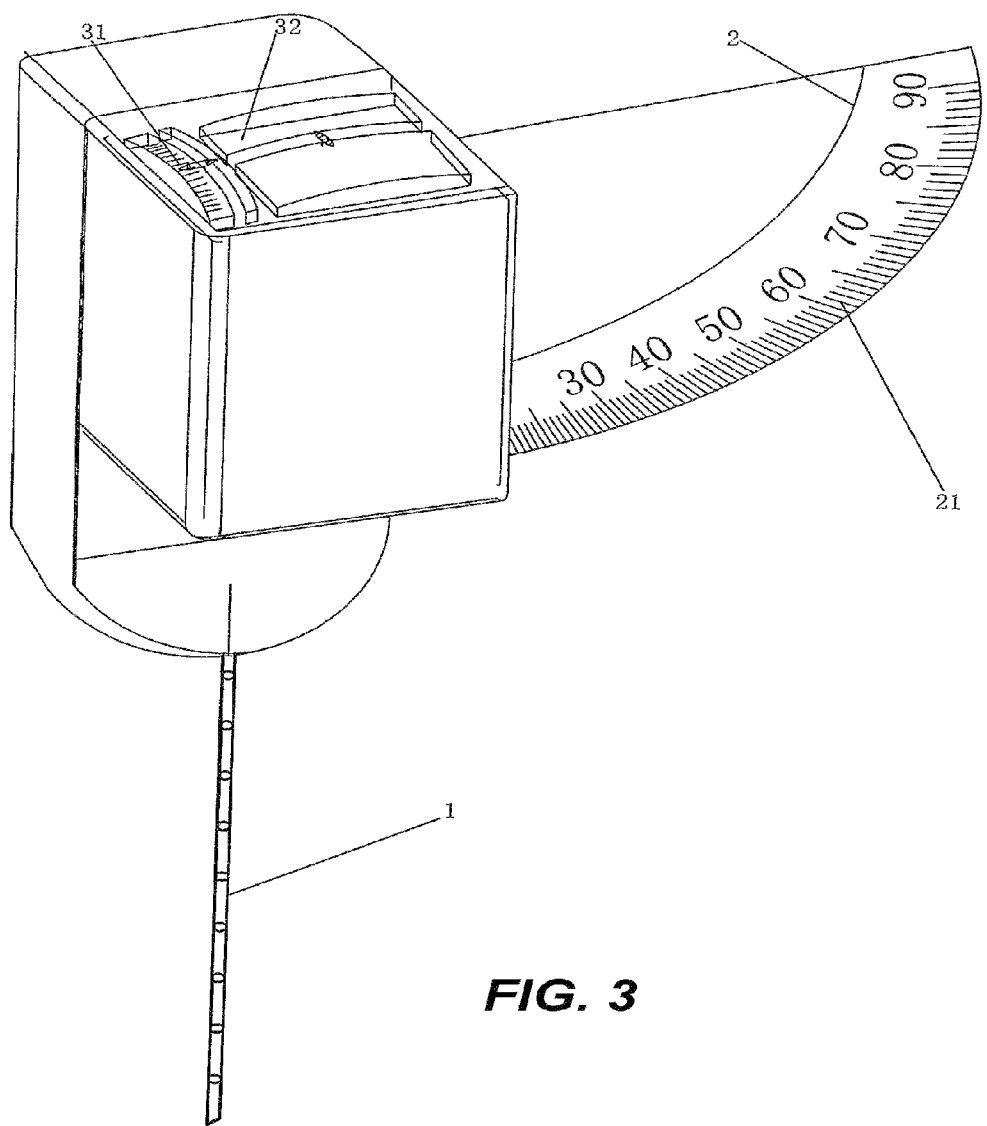
FIG. 3 is a schematic view of an embodiment of the invention showing that needle-entering angle reference line leveling component and puncturing layer leveling component are installed within the same casing.
Figure 4:
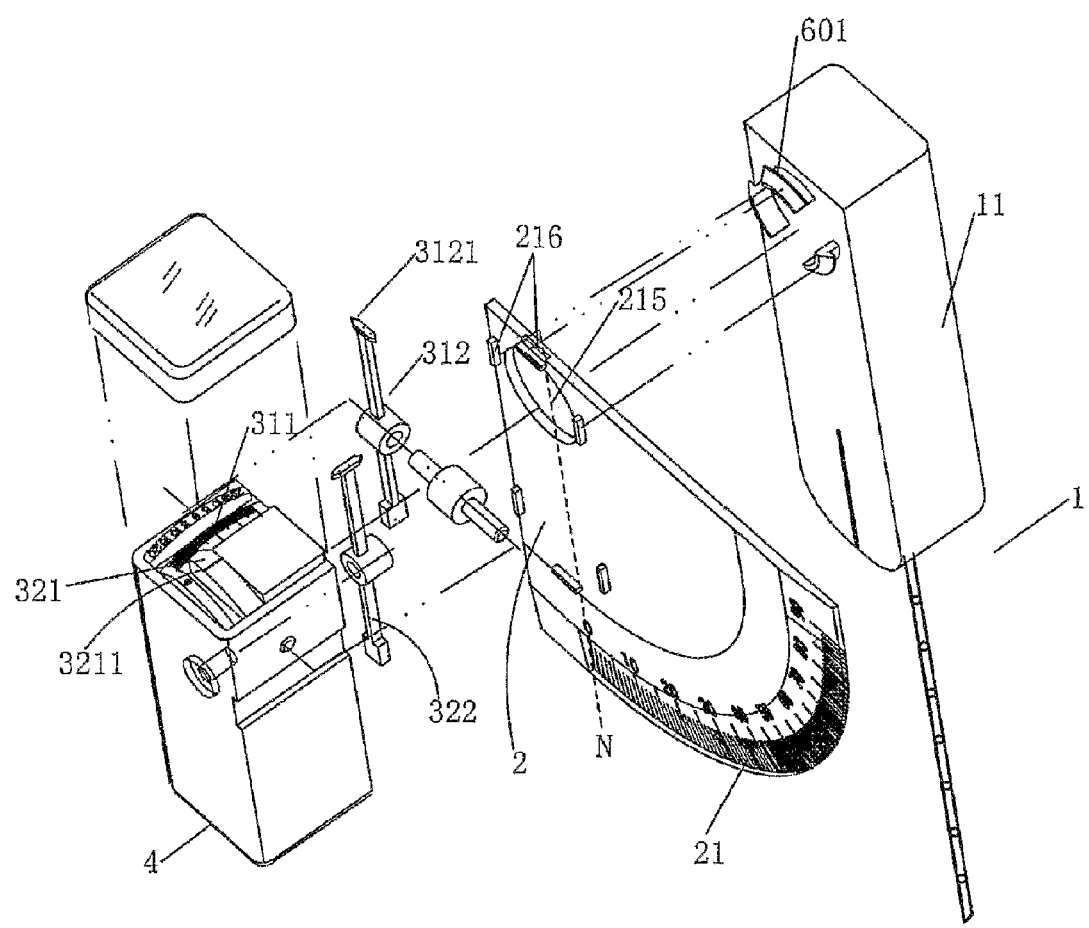
FIG. 4 is a decomposition view of FIG. 3.

Based on above principles, the disclosed puncturing needle guiding device as shown in FIGS. 3, 4 include the puncturing needle 1 and the guiding device for fixing puncturing needle and indicating the needle-entering angle of puncturing needle angle. Said guiding device includes: a needle-entering angle guide means 2, said puncturing needle 1 is rotably connected with guide means 2 via a connecting mechanism; said guide means 2 is made with a needle-entering angle reference line N and an angle indicating device 21 for indicating the intersected angle between actual needle-entering direction of the puncturing needle and the reference line; a puncturing layer leveling component 31 having an angle indicating device 311 for indicating the deviatingly rotated angle of the puncturing needle rotating plane thereby allowing the needle-entering layer C of puncturing needle 1 to be parallel to or superposed with scanning layer A of scanning equipment or puncturing layer B on human body. In usage, said needle-entering layer is the rotating plane of puncturing needle 1. Said guide means 2 is sidely affixed to the puncturing layer leveling component 31, and the deviating angle rotating axis of the angle indicating device of said puncturing layer leveling component 31 for indicating the deviatingly rotated angle of the puncturing needle rotating plane is parallel to said guide means.

Figure 6:
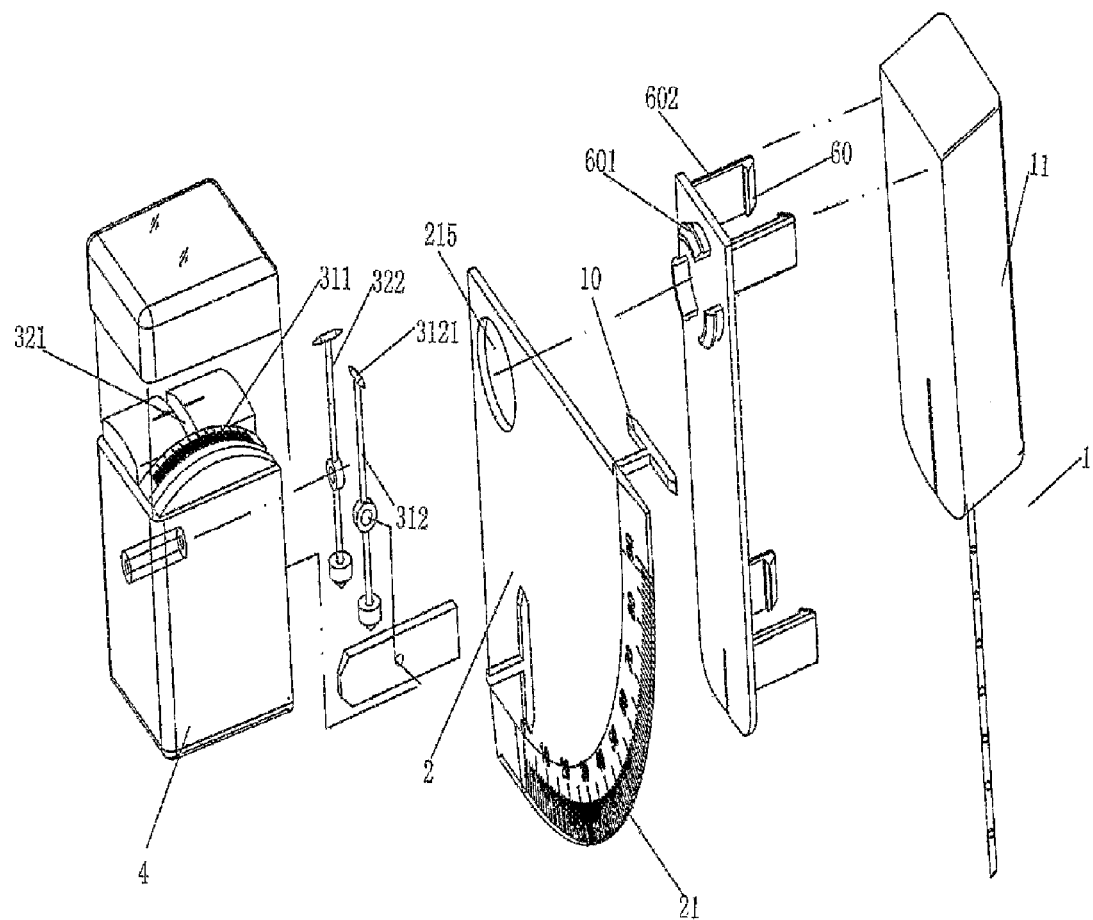
FIG. 6 is a decomposition view of FIG. 5.

A needle-entering reference line leveling component 32 to adjust the needle-entering angle reference line on the guide means to be on the same plane of the hammer weight line, wherein said needle-entering reference line leveling component 32 is made with an angle indicating device 321 having its deviatingly rotated axis being perpendicular to the deviating angle rotating axis of the angle indicating device 311 on said puncturing layer leveling component 31;

Said guiding device is further made with a leveling benchmark 10 for instructing the horizontal line on rotating puncturing plane to be parallel to the needle-entering layer (referring to FIG. 6).

The angle indicating devices for said guide means 2, puncturing layer leveling component 31, reference line leveling component 32 can be digit type angle indicator, or mechanical type angle indicator marked with angle scales and pointer, or bubble type level gauge (referring to FIG. 8); no matters how the puncturing needle guiding device is inclined, superposition or parallel of the needle-entering plane and puncturing plane as well as superposition or parallel of the needle-entering reference line of needle-entering angle θ' and needle-entering reference line of needle-entering angle θ by the scanning and detecting equipment are always ensured by the angle adjustment via angle indicating devices of puncturing layer leveling component 31 and reference line leveling component 32.

In the embodiment shown by the figure, said guide means 2 is an angle indicating device of mechanical type having a flat plate angle indicator 21 with angle scale; rotating center of said puncturing needle 1 being used as the pointer for the angle indicator is superposed with the angle measuring center of the flat plate angle indicator 21, the rotating plane of puncturing needle 1 is parallel to the plate surface of said flat plate angle indicator, and said puncturing angle reference line N being passing through the rotating center of said puncturing needle is on the plate surface of said flat plate angle indicator.

In the embodiment shown by the figure, the angle indicating device 311 of said puncturing layer leveling component 31 is a mechanical type angle indicator, said mechanical type angle indicator is a hammer weight type swing pointer angle indicator comprising angle indicating plate 312 and hammer weight swing pointer 312 being concentrically installed with the circle of angle indicating plate; wherein, the swing plane of the hammer weight swing pointer of said puncturing layer leveling component is perpendicular to the plate surface of flat plate angle indicator of said guide means 2;

In the embodiment shown by the figure, the angle indicating device on said reference line leveling component 32 is a mechanical type angle indicator. Said mechanical type angle indicator is a is a hammer weight type swing pointer angle indicator comprising angle indicating plate 312 and hammer weight swing pointer 322; wherein, the swing plane of the hammer weight swing pointer of said puncturing layer leveling component 31 is perpendicular to the swing plane of the hammer weight swing pointer angle indicator of the reference line leveling component 32.

In present invention, said puncturing needle is through a connecting mechanism to rotably connect with the flat plate needle-entering angle indicator of the guide means on the same axis center; said flat plate angle indicator for needle-entering angle indication is centrally made with a center hole 215 or locking rail 216 being connected with puncturing needle at the center portion or near to the center portion thereof.

Figure 5:
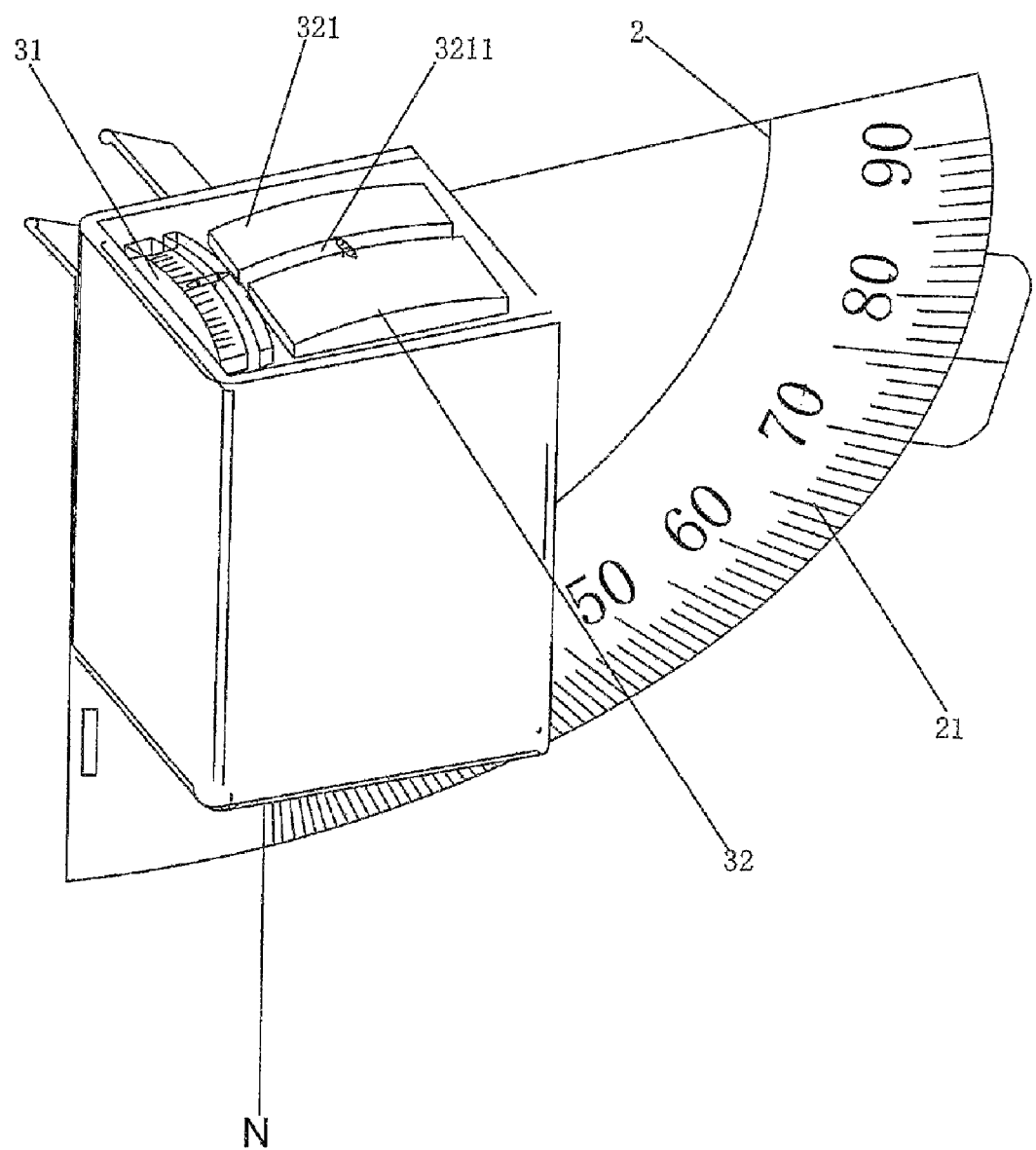
FIG. 5 is a schematic view of another embodiment of FIG. 3.
Figure 7:
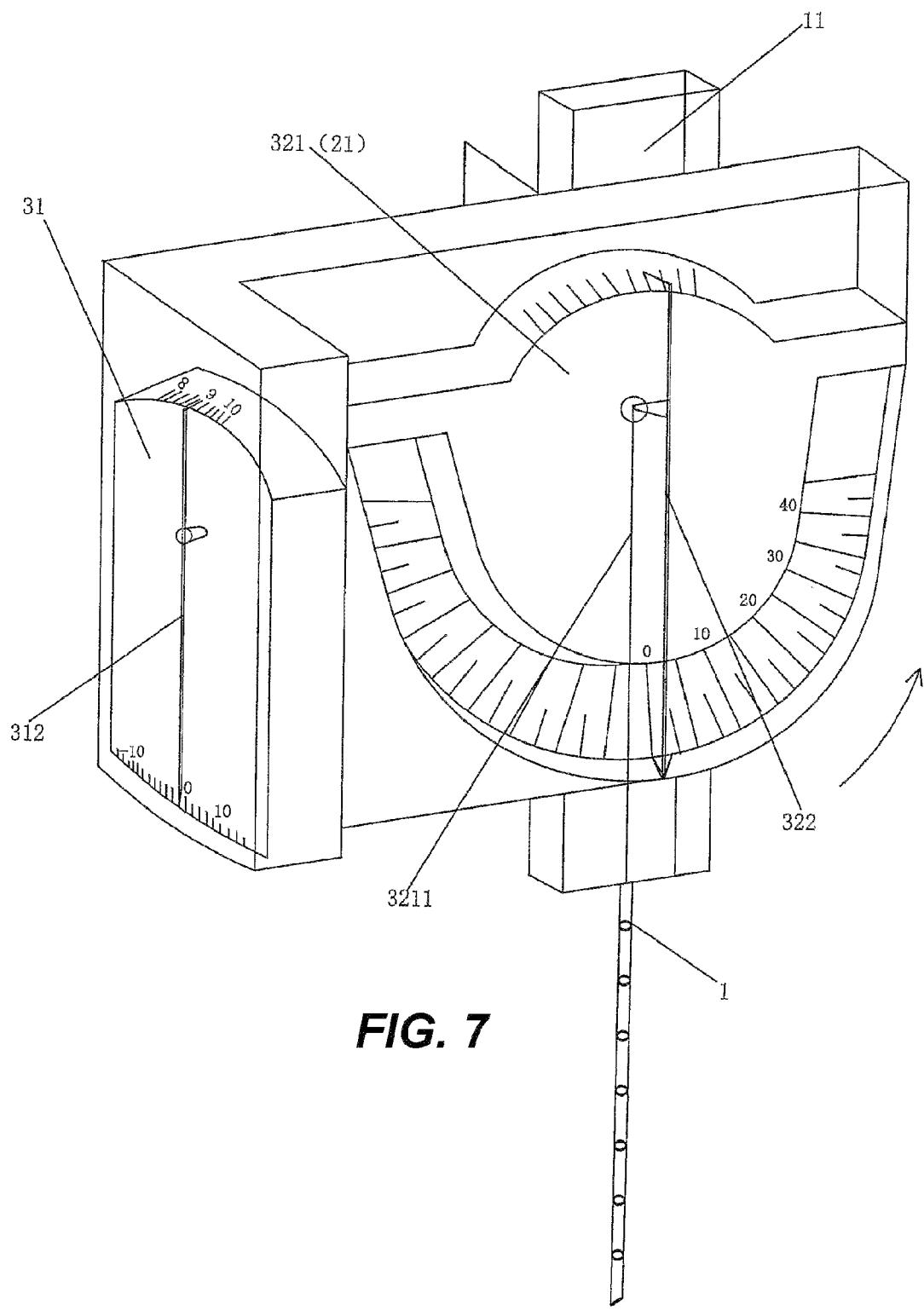
FIG. 7 is a schematic view showing that guide means, reference line leveling component and puncturing layer leveling component are installed on or inside the casing.

The angle scale of the flat plate needle-entering angle indicator 21 of the present invention is 0-360°, preferably 0-180° as shown in FIG. 7 or can be 0-90° as shown in FIGS. 3-5. The rotating angle of said puncturing needle 1 following the flat plat needle-entering angle indicator 21 of guide means is 0-360°, preferably 0-180°, or 0-90° as shown in FIGS. 3-5. The flat plate needle-entering angle indicator 21 is preferably an upside down protractor.

If the needle-entering reference line leveling component is a bubble type level gauge, the installation method for the bubble type level gauge can be referred to U.S. Pat. No. 5,196,019, the axis of the preferred bubble type level gauge is simultaneously parallel to horizontal plane and first rotating plane. As referring to FIG. 8, when bubble 323 is at the center position, the bubble center line being extended downwardly perpendicularly is parallel to the line on flat plate needle-entering angle indicator 21 having its projected line to be superposed with the center line N of the flat plate needle-entering angle indicator 21, i.e. center line N is the needle-entering reference line, while the projection of the bubble type level gauge marking line on the flat plat needle-entering angle indicator 21 can also be used as the reference, said needle-entering angle θ is the rotated angle of puncturing needle relative to the reference line, wherein the needle-entering angle θ is provided by the detected results of the detecting equipment.

Similarly, if the needle-entering reference line leveling component is the reference line leveling hammer weight 322, centerline of the preferred flat plate needle-entering angle indicator 21 is the needle-entering angle reference line, said needle-entering angle θ is the rotated angle of puncturing needle relative to the reference line, wherein the needle-entering angle θ is provided by the detected results of the detecting equipment.

For puncturing layer leveling components, said puncturing layer angle indicator 31 is a puncturing layer leveling hammer weight 312 having the pointer 3121, said puncturing layer leveling hammer weight 312 is pivotally installed on the angle indicating plate 311 of puncturing layer leveling component, and if hammer weight is pointing to the 0 scale (center) of angle indicating plate 311, it means that the detecting equipment is perpendicular to the detected human body, and is more preferably perpendicular to the longitudinal direction of the detected body. The scale of the puncturing layer angle indicating plate 311 is started from 0 degree and extended to the two sides of plate to less than 90 degree, less than 45 degree in general, or less than 30 degree which is more commonly seen.

The angle indicating device of the puncturing layer leveling component can also be the angle indicating or measuring devices in present arts.

The flat plate needle-entering angle indicator 21 of guide means is made with a T shaped leveling benchmark 10 being aimed at scanning layer for marking direction of Y' axis of guide means (puncturing plane) as shown in FIG. 6. The axis of leveling benchmark 10 is on the puncturing needle rotating plane, wherein the benchmark is connected to the angle indicating base plate via a column to form the T shaped protruding frame, wherein number of the T shaped protruding frames is 1-2 pieces as shown in FIG. 6.

The flat plate needle-entering angle indicator 21 is made with a center hole 215 and/or locking rail or locking slot 216 for allowing puncturing needle 1 to rotate on the flat plate needle-entering angle indicator 21. (Referring to FIG. 4, FIG. 13).

In the embodiment of the invention as shown in FIG. 4, the needle holder 11 of puncturing needle 1 is rotably connected with guide means 2 via a connecting mechanism 60. The connecting mechanism 60 for connecting puncturing needle 1 and guide means being installed on needle holder 11 is passing through the center hole 215 at central portion of flat plate needle-entering angle indicator 21 to ratably lock the needle holder 11 of puncturing needle 1 to the locking rail 216, or the connecting piece of locking slot 216 on flat plate needle-entering angle indicator 21, or spindle connection can also be adopted, said connecting pieces can be independent components as shown in FIG. 6, wherein two end portions of the independent component are respectively made with a locking hook 601 and locking claw 602, and said locking hook 601 being preferable to be continuous or intermittent shape is locked on the flat plate needle-entering angle indicator 21 at one end thereof via central hole 215 on the flat plate needle-entering angle indicator 21, and the locking claw 602 at the other end is locked with the puncturing needle holder 11; the puncturing needle is preferably translated along the locking slot of lock claw 602 to allow puncturing needle to reach the needle-entering depth of the scanning and detecting equipment, so as to further promote the accuracy of needle-entering by eliminating human factor influences. Under this circumstance, the puncturing needle of existing art comprising a needle 12, a needle holder 11 can be adopted; said needle holder 11 is a puncturing needle type or column type injector; said connecting mechanism is a locking connecting piece being affixed to the needle holder 11, wherein needle holder 11 having locking type connecting piece is lockingly combined with the locking rail or locking slot 216 on flat plate needle-entering angle indicator 21. Said connecting mechanism 60 can also adopt the spindle connection of existing art.

As shown in FIGS. 4 & 6, said guiding device is made with a top open rectangular casing, said guide means 2 of needle-entering angle indicator is sidely affixed to said rectangular casing 4, said puncturing layer leveling component 31 and reference line leveling component 32 are installed inside the casing, the angle indicating devices of said puncturing layer leveling component 31 and reference line leveling component 32 are exposed via the top opening; and said casing opening is lockingly covered by a transparent cover.

Figure 8:
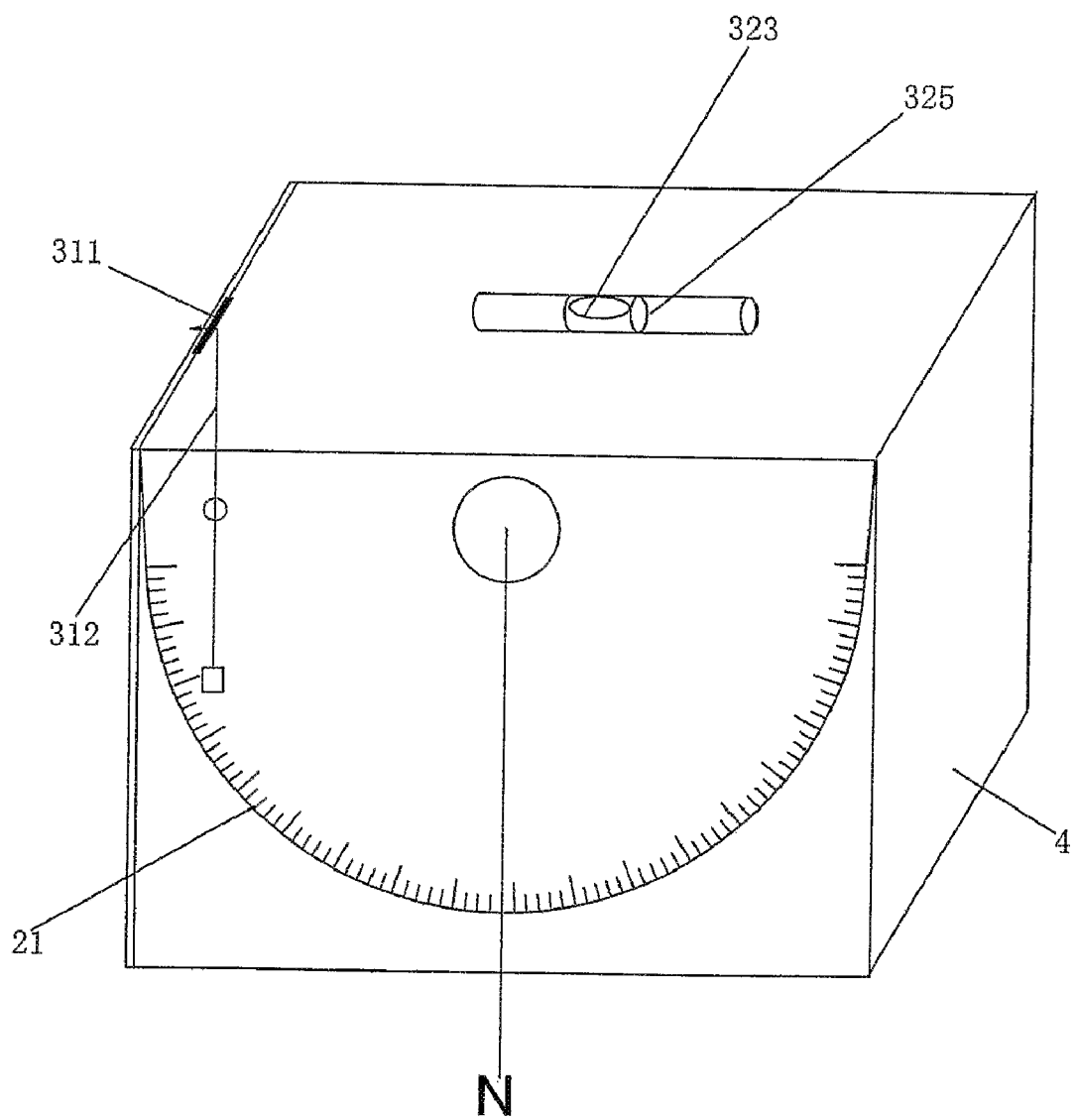
FIG. 8 is the schematic view of another embodiment of FIG. 7.

FIG. 8 is an embodiment of the present invention, wherein guide means 2, reference line leveling component 32 and puncturing layer leveling component 31 are installed on or inside a casing 4, the flat plate needle-entering angle indicator 21 is one side of the casing having angle scales, when the casing is made of transparent material, said angle scale can be marked on either side of the first side wall; the reference line leveling component 32 is installed on a plane perpendicular to flat plate needle-entering angle indicator 21, when reference line leveling component 32 is at 0 degree, the centerline N of flat plate needle-entering angle indicator 21 is the reference line of needle-entering angle, wherein said needle-entering angle θ is the rotating deviation of the puncturing needle relative to the reference line; a puncturing layer angle indicating plate 311 of puncturing layer leveling component 31 being installed on the side wall being perpendicular to flat plate needle-entering angle indicator 21 of guide means is marked with angle scales, the central scaling line is 0 degree, and is extended to the two sides to less than 90 degree, less than 45 degree in general, or less than 30 degree which is more commonly seen. The puncturing layer angle indicating device 312 being a puncturing layer leveling hammer weight with pointer 3121 is pivotally installed on the side wall (puncturing layer angle indicating plate 311), when hammer weight points to 0 (center) scale of puncturing layer angle indicator, it means that the scanning and detecting equipment is perpendicular to detected human body. The locking hook on puncturing needle holder is rotably connected to the locking rail 216 of flat plate needle-entering angle indicator 21, wherein projection line of puncturing needle axis on the flat plate needle-entering angle indicator 21 is superposed with the angle centerline N of flat plate needle-entering angle indicator 21, while the rotating axis of puncturing needle and the axis of the flat plate needle-entering angle indicator of guide means are preferably to be the same. The independent connecting structure shown in FIG. 6 is also applicable as an option. The puncturing needle holder can also be rotably connected to another wall being parallel to the first side wall via a connecting mechanism to be another option, similar to the one shown in FIG. 7.

FIG. 7 shows another embodiment of the invention, said guiding device is made with a L type right angle bended plate 33 comprising two flat plates, said needle-entering angle guide means 2 and said reference line leveling component 32 are installed on one of the flat plate 331 on the L type right angle bending plate 33, and angle swing planes of said needle-entering guiding means 2 and said reference line leveling component 32 are parallel to the surface of said flat plate 331; said puncturing layer leveling component 31 is installed on another flat plate 332 of the L type right angle bending plate, and the angle swing plane of said puncturing layer leveling component is parallel to the surface of another flat plate 332. Further, the angle indicating plate 321 of the reference line leveling component and the flat plate needle-entering angle indicator of needle-entering guide means commonly use the same central scaling line 3211, i.e. the 0 scale in FIG. 7. The central scaling line 3211 indicated by the pointer of hammer weight pointer structure 322 on the flat plate needle-entering angle indicator 21 is the needle-entering reference line, when scale of the flat plate needle-entering angle indicator 21 of the guide means is 0~180°, the pointer of hammer weight indicating structure 322 of the preferred reference line leveling component 32 is pointed to the 90° line on flat plate needle-entering angle indicator 21, and at this moment, the 90° scaling line on the flat plate needle-entering angle indicator 21 of the guide means is the reference line for needle-entering angle of the flat plate needle-entering angle indicator of the guide means; while when the scale of the flat plate angle indicator of guide means is 180° of 90°-0°-90°, the pointer of hammer weight indicating structure 322 of the preferred reference line leveling component 32 is pointed to and is superposed with or parallel to the 0° position line on the flat plate needle-entering angle indicator, and at this moment, the 90° scaling line or 0° scaling line on the flat plate needle-entering angle indicator of the guide means are respectively the needle-entering angle reference lines of the flat plate needle-entering angle indicator of guide means.

Figure 9:
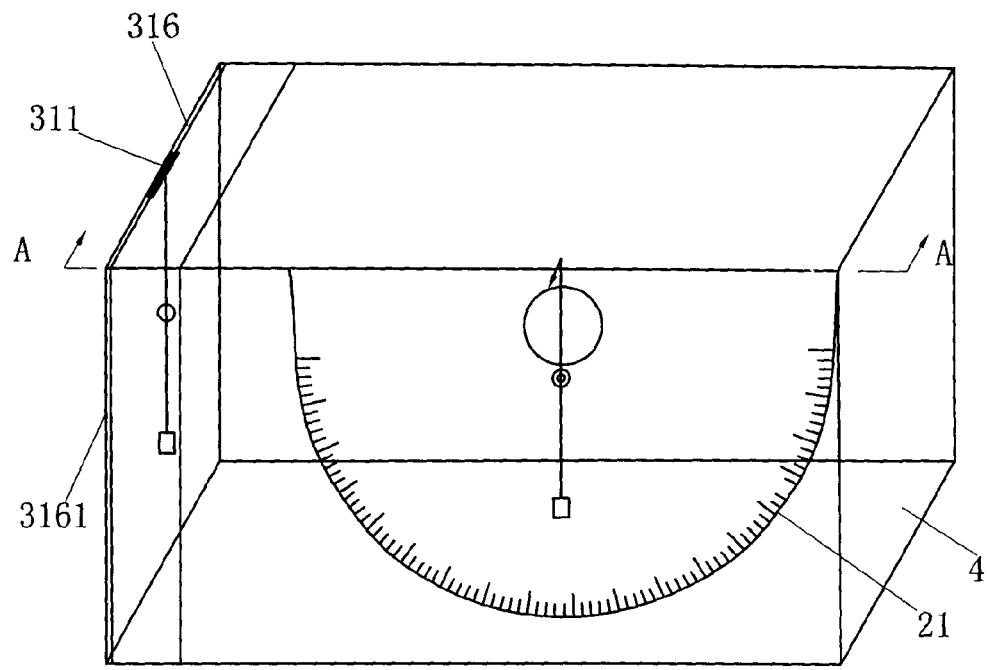
FIG. 9 is a schematic view showing that reference line leveling component as shown in FIG. 8 is a hammer weight.
Figure 9A:
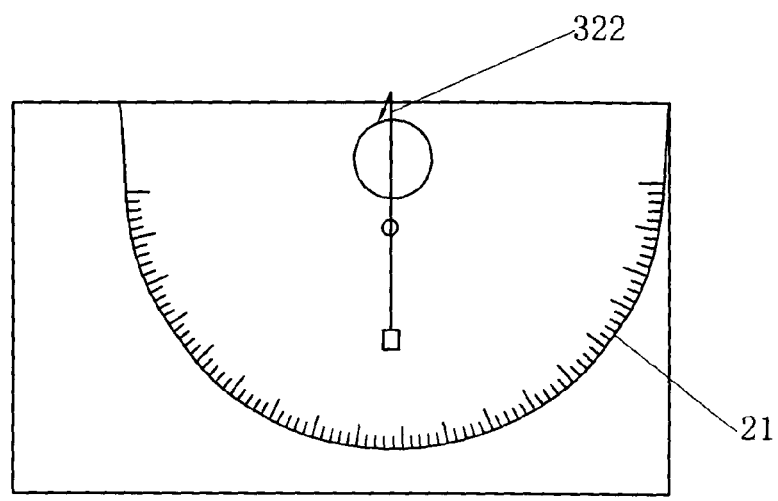
FIG. 9a is the cross-sectional view A-A of FIG. 9.

As a variation to aforesaid embodiment, the reference line leveling component 32 can be the swingable reference line leveling hammer weight 322. As shown in FIG. 9, the reference line leveling hammer weight 322 being installed inside casing 4 is pivotally installed on the inner/external side of the side wall of the flat plate needle-entering angle indicator 21, or on the other side wall of said casing in parallel and facing to the said side wall, when reference line leveling hammer weight 322 is pivotally installed on the inner/outer side of said side wall with inner side in preference, said side wall (flat plate needle-entering angle indicator 21) is also used as the base plate for reference line leveling component 32; when the reference line leveling hammer weight 322 is pivotally installed on the other side wall of the casing with preference in inner side, said side wall is also marked with angle scaling lines, wherein the angle scale is at least a central marking sign, or can be done by installing a horizontal bar between two neighboring side walls of the guide means inside the casing, the reference line leveling hammer weight 322 is installed on the horizontal bar (no shown in the figure), is through a directional valve to install inside casing 4 that can be easily done by technicians in this field. Under this circumstance, when the pointer of reference line leveling hammer weight 322 is pointed to the center of angle indicating plate of reference line leveling component 32, the axis projection of reference line leveling hammer weight 322 on the flat plate needle-entering angle indicator 21 is superposed with the centerline N of flat plate needle-entering angle indicator 21, and the centerline of flat plate needle-entering angle indicator 21 is the reference line of the needle-entering angle. The connection method between puncturing needle 1 and the casing is the same as described in aforesaid embodiments. Said needle-entering angle θ is the angle of puncturing needle relative to the deviatingly rotated angle, wherein needle-entering angle θ is obtained from the scanning results of the scanning and detecting equipments.

When puncturing needle guiding device of the invention is rotated to inclined angle α as the same as the one of scanning equipment, the angle indicated by the pointer 3121 of puncturing layer leveling hammer weight 312 on puncturing layer angle indicating plate 311 is also α, and if the α value is the inclined angle of scanning and detecting equipment, i.e. the inclined angle of scanning layer of the scanning and detecting equipment, then the plane of puncturing needle guiding device 1 is superposed with the scanning layer of scanning and detecting equipment; at this moment, puncturing needle 1 is rotated according to the needle-entering angle θ provided by the scanning and detecting equipment after scanning, then point of puncturing needle 1 is placed to the needle-entering point confirmed by the scanning and detecting equipment after scanning, next, puncturing is performed by adjusting hammer weight or level gauge of reference line leveling component to central position, and the needle is punctured according to the marked size on puncturing needle to needle-entering depth, then the puncturing needle can hit the focus point accurately.

As an option, the puncturing layer leveling component can be further installed with a hood 316 besides having puncturing layer angle indicating plate 311 and puncturing layer leveling hammer weight 312, and if side wall 3161 of the hood 316 is perpendicular to flat plate needle-entering angle indicator 21, the puncturing layer angle indicating plate 311 and puncturing layer leveling hammer weight 312 can be installed on said side wall 3161 to also achieve the puncturing guiding function as shown in FIG. 9. Similarly, if installing conditions of bubble type level gauge 325 are satisfied, the bubble type level gauge 325 not only can be installed on aforesaid casing, but also can be installed on any plane being parallel to flat plate needle-entering angle indicator 21.

FIGS. 3-4 are schematic views of puncturing needle guiding device showing that reference line leveling component 32 and puncturing layer leveling component 31 are installed within the same casing 4, puncturing needle 1 is rotably connected with flat plate needle-entering angle indicator 21 of guide means 2 via locking hook 601 on the needle holder, the flat plate needle-entering angle indicator 21 is made with a protruding piece for inserting into the matching slot of casing 4 (not shown in the figure), and flat plate needle-entering angle indicator 21 can be directly affixed to casing 4.

FIGS. 5-6 are schematic views of a variation of the puncturing needle guiding device of the invention showing that reference line leveling component 32 and puncturing layer leveling component 31 are installed within the same casing, wherein puncturing needle 1 is rotably connected to guide means 2 via an independent connecting mechanism 60. The guide means is made with a T type protruding frame 10.

Figure 12:
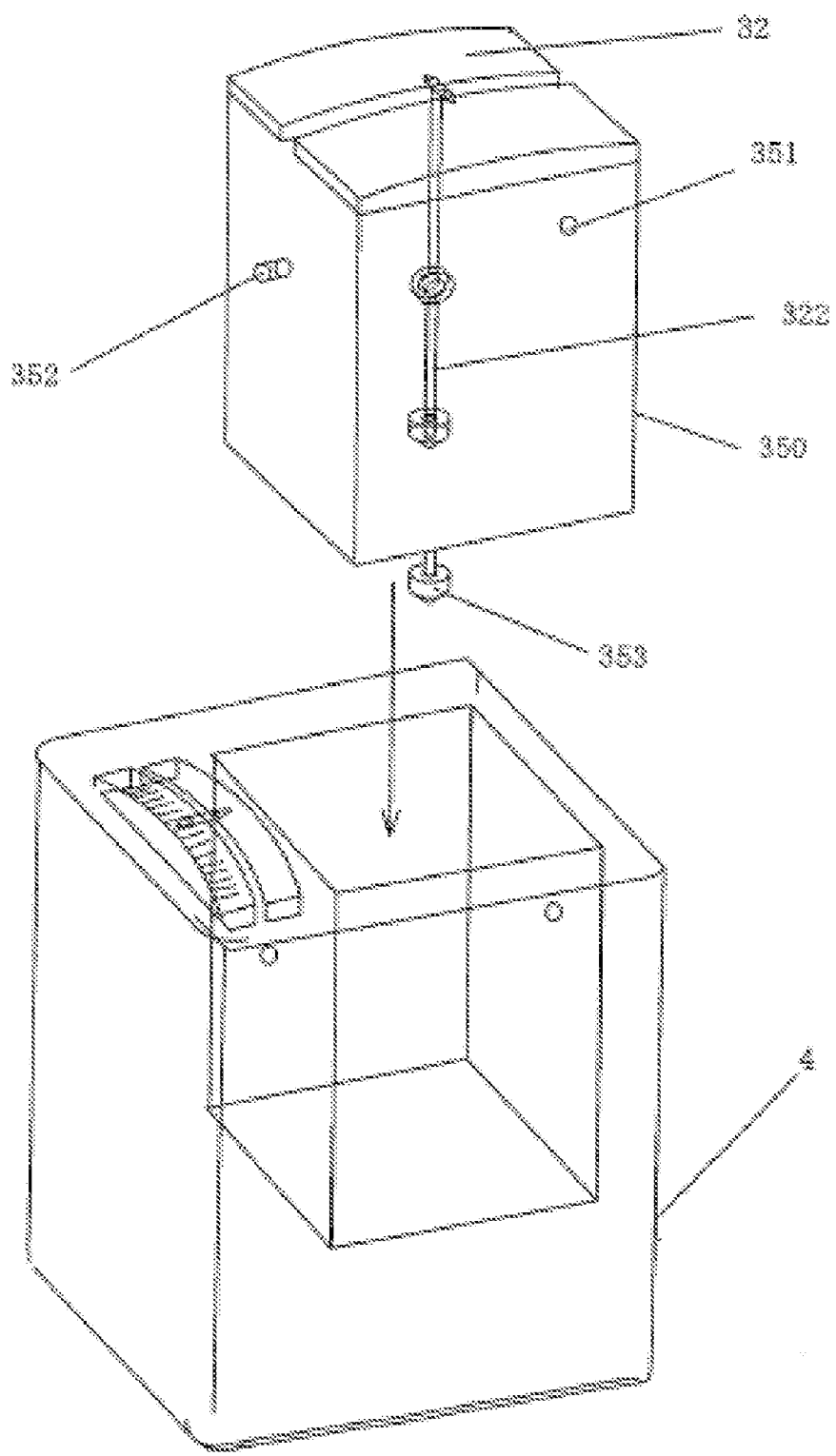
FIG. 12 is a schematic view of another embodiment of the leveling component.

FIG. 12 is a schematic view shows the embodiment of reference line leveling component 32 being installed in casing 4, wherein for ensuring that reference leveling hammer weight 322 is always perpendicular to the horizontal plane in the embodiment, the reference line leveling hammer weight 322 and angle indicating plate 321 of reference line leveling component are installed inside a reference leveling casing 350, the reference leveling casing 350 is installed with a hammer weight 353 at the bottom center thereof, and the two side walls of the reference leveling casing 350 being perpendicular to angle indicating plate 321 of reference leveling component are respectively installed with two spindles 351, 352 at the center thereof, and the ends of spindles 351, 352 are installed on the casing 4 by adopting the method of existing art. Or, the casing is made with a vertical plane, and the end of spindle 352 is installed on the vertical plane (not shown in the figure) by adopting the method of existing art so as to ensure that reference leveling hammer weight 322 is always perpendicular to the horizontal plane.

Figure 13:
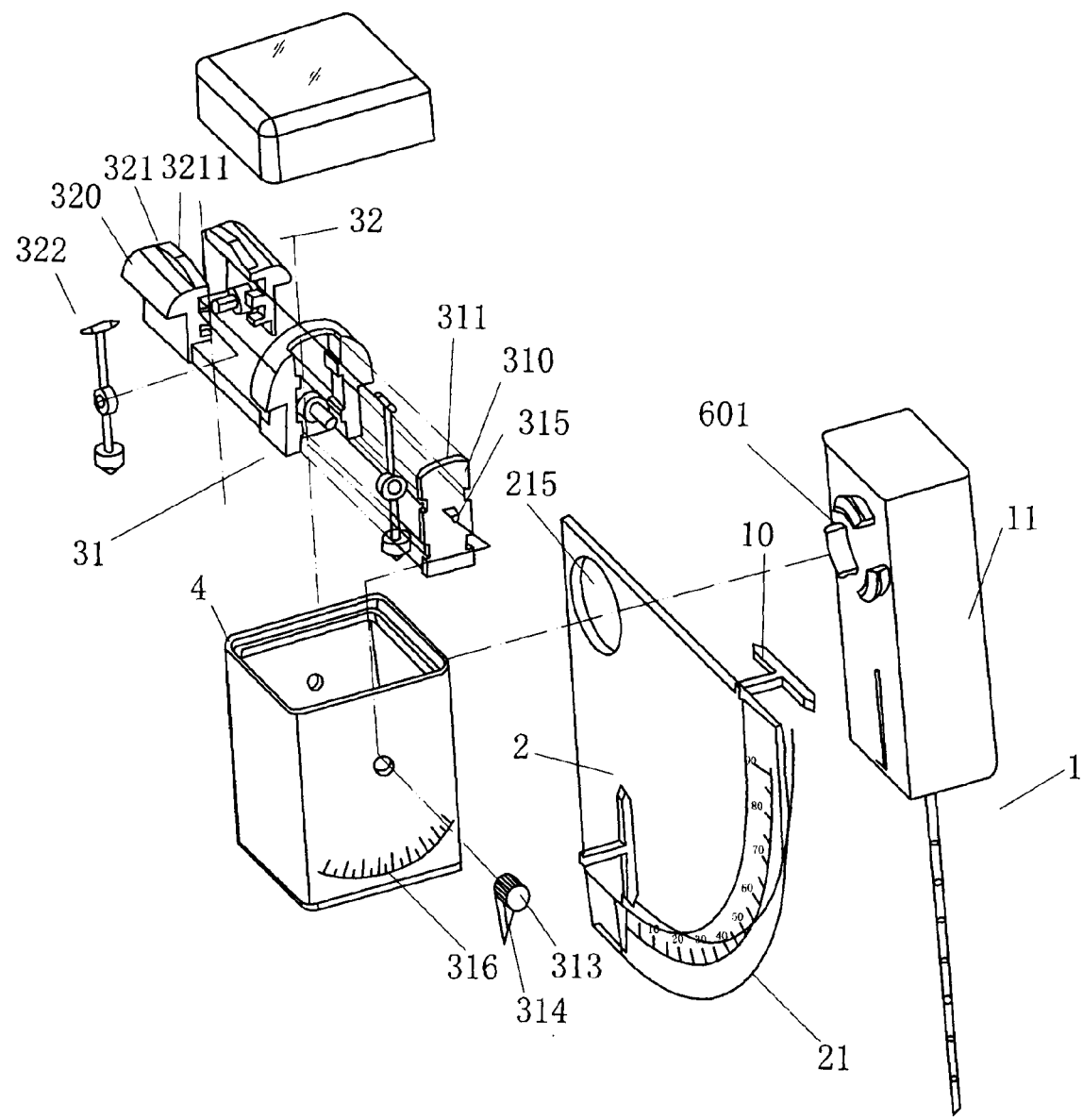
FIG. 13 is a schematic view of one more embodiment of the leveling component.

FIG. 13 shows an embodiment of the puncturing needle guiding device, wherein puncturing layer leveling component 31 and reference line leveling component 32 of the guide means are mutually fixed, a rotating spindle 315 is at the same axis with the angle rotating axis of puncturing layer leveling component, said puncturing layer leveling component 31 and reference line leveling component 32 being integrally fixed is pivotally installed on said casing 4 with rotating spindle as the pivotal axis, said rotating spindle 315 is protrudingly extended out of casing 4, wherein the external surface being installed with protrudingly extended rotating spindle is made with rotating angle scale 316 for the rotating spindle, and a knob 313 with pointer 314 is affixed to the said protrudingly extended rotating spindle.

The second aspect of the present invention is related to the application of the guided puncturing needle and puncturing guiding method, wherein it includes the following steps:

1. The 3D coordinates of the focus point position 0 is detected by CT or MRI scanning device to confirm the puncturing sectional layer Y0Z, and the skin needle-entering point L and projection line of scanning layer on the body surface; wherein the needle-entering angle and depth is calculated by the angle of the line connecting the puncturing hitting focus point and skin needle-entrance point relative to horizontal line, or vertical line of horizontal line and the length of the line;
2. The puncturing needle is installed on the needle-entering angle indicating plate of the guide means;
3. Leveling the puncturing needle-entering angle: the needle-entering angle of the puncturing needle is adjusted on the angle scale plate of guide means along the puncturing needle axis to corresponding angle according to the needle-entering angle confirmed by CT or MRI scanning device;
4. The needle point of puncturing needle is aimed at the skin needle-entering point confirmed by the scanning and detecting equipment, thereby allowing the needle-entering angle hammer weight of reference leveling component is pointed to the 0° line of the angle indicating base plate, or the pointer of hammer weight is pointed to 0 scale;
5. The puncturing needle guiding device is deviatingly rotated according to the inclined angle of CT gantry or the deviatingly rotating angle of MRI scanning device until reaching the same angle as the inclined angle α of CT gantry or MRI scanning device displayed by the angle display device of scanning layer leveling component;
6. The scanning layer leveling benchmark is aimed at the axis of puncturing needle and projection line of scanning layer on body surface; and
7. The needle is punctured into the human body till the needle-entering depth confirmed by CT or MRI scanning devices so as to hit the focus point.

The puncturing guiding method of the present invention further includes confirmation on the CT scanning effectiveness.

The angle scale of said flat plate needle-entering angle indicator is 0-360°, preferably 0-180°, and can also be 0-90°.

As an option, the reference line leveling component as shown in FIGS. 3-6 can be the bubble type level gauge 325, such as that bubble type level gauge 325 as shown in FIG. 8 is installed at the center of angle indicating plate 321 of the reference line leveling component, wherein the upper wall of the flat plate needle-entering angle indicator 21 of certain thickness allow the downward bubble centerline being parallel to flat plate needle-entering angle indicator 21 having its projection line on the flat plate needle-entering angle indicator 21 to be superposed with the centerline N of flat plate needle-entering angle indicator 21.

The top surface of the angle indicating plate in the above described embodiments is preferably to be an arc shape, said angle scaling lines are made on the top surface so that the pointer being connected on top of the matched hammer weight indicating component can be freely slid along the arc shaped top surface of each base plate. The casing and/or base plate are preferably made of transparent material, so that movement of the pointer of the hammer weight type indicating device relative to the 0° scale of base plate can be seen through the casing.

In usage, the 3D coordinates of focus point position 0 is detected and puncturing layer Y0Z is confirmed through the CT or MRI scanning device, and the skin needle-entering point L and projection line of scanning layer on the human body are marked on the human body. The guided puncturing needle 1 of proper diameter is selected, or the puncturing needle of existing art is installed on the connecting mechanism 60 via the needle holder, and is further connected to the flat plate needle-entering angle indicator 21 of guide means 2, then said puncturing needle guiding device is held by hand to allow the puncturing needle to follow along the puncturing needle axis for adjusting the needle-entering angle to corresponding angle θ on the angle scale plate of guide means according to the needle-entering angle confirmed by CT or MRI scanning devices; next, the needle point of puncturing needle is aimed at the skin needle-entering point confirmed by scanning and detecting equipment, the needle-entering angle hammer weight of reference line leveling component is pointed to the 0° line (central scaling line) on angle indicating base plate, or the hammer weight pointer is pointed to 0° scale. If the reference line leveling component is a bubble type level gauge, the bubble of the bubble type level gauge is positioned at the center, then centerline of flat plate needle-entering angle indicator 21 is the needle-entering angle reference line; the puncturing needle guiding device is deviatingly rotated according to the inclined angle of CT gantry or the deviatingly rotating angle of MRI scanning device until reaching the same angle as the inclined angle α of CT gantry or MRI scanning device displayed by the angle display device of scanning layer leveling component. At this moment, puncturing needle 1 of puncturing needle guiding device is on the scanning layer scanned by the CT or MRI scanning device, and it is also the puncturing layer of the puncturing needle, i.e. the needle-entering puncturing layer B is completely superposed with scanning layer A, therefore, by following the needle-entering depth confirmed by the CT or MRI scanning device to puncture the needle and further scanned by the CT or MRI scanning device afterward, the accurate puncturing needle hitting on the focus point can be confirmed.

Figure 10:
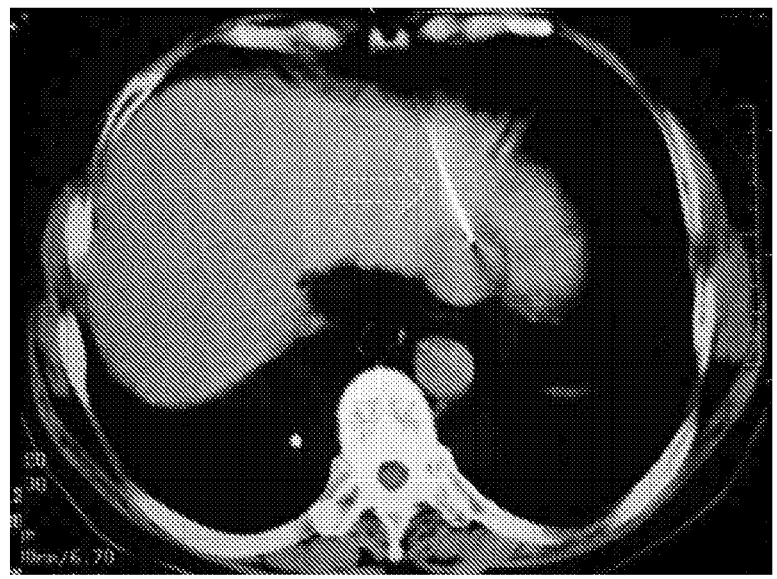
FIG. 10 is a scanned view of needle-entering result by CT scanning after puncturing by adopting the method of existing art.
Figure 11:
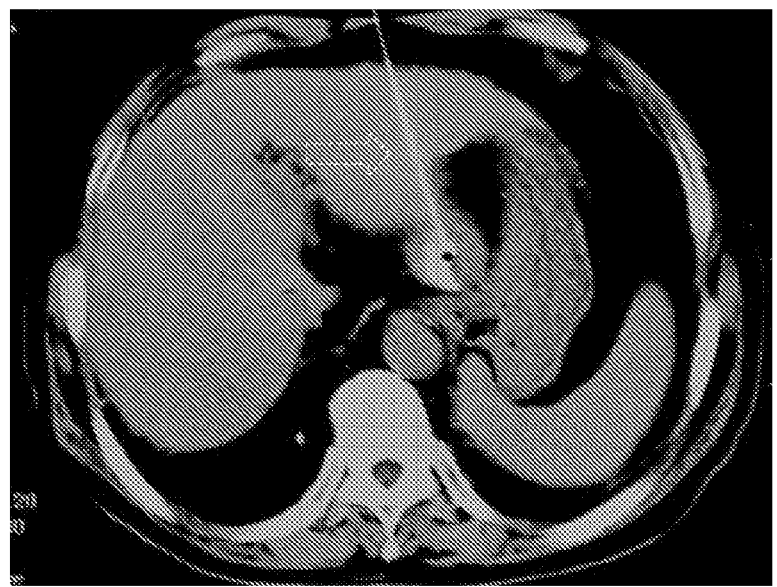
FIG. 11 is a scanned view of needle-entering result by CT scanning after puncturing by adopting the puncturing needle and puncturing guiding method of the present invention.

FIGS. 10 & 11 are scanning views of needle-entering result by CT scanning after puncturing by respectively adopting the method of existing art as well as the puncturing needle and puncturing guiding method of the present invention. As can be seen from the comparisons, for puncturing by adopting the method of existing art, only part of the puncturing needle can be seen by CT scanning (as seen by the arrow direction), As clear observation on whole needle is unable to obtain, the needle-entering route and whether the puncturing needle hit the focus point or not is unable to be understood; while for the puncturing by adopting the guided puncturing needle and puncturing guiding method of the present invention, as the puncturing is performed according to CT scanning layer, i.e. the needle-entering puncturing layer, the needle-entering layer is then completely superposed with CT scanning layer; hence, after puncturing needle hits the focus point, the accurate target hitting by the puncturing needle as well as the whole length of puncturing needle can be simultaneously seen by re-running the CT scanning, so that the doctor not only is able to understand the puncturing hitting target status, but is also able to clearly see the whole needle-entering path of the puncturing needle including whether there are blood vessel nerves or not, bone qualities and other important organs, etc. and is able to clearly see the status of tissue biopsy and various therapies under puncturing (FIG. 11 and arrowed direction) and it explains that the guided puncturing needle and puncturing guiding method of the present invention is accurate, convenient and easy for operation.

The protected scope of the present invention is not limited to the above described embodiments only, wherein any variations within the range of purposes and principles of the present invention shall be included in the protected scope of the invention.

The puncturing needle guiding device of the present invention not only can be used for puncturing inside the scanning layer but also can be used as the diagnosis and therapy guiding device for pathological biopsy, medicine injection, catheter indwelling, bone opening, and implanting medicine or seeds as well as physical therapies such as RF, microwave and the like; whereas it is only required to replace the puncturing needle in usage according to different purposes of applications, then the target-hitting can be achieved accurately rapidly.

As summarized from the above descriptions, the puncturing needle guiding device of the invention mainly includes: the present invention has the puncturing layer leveling component and needle-entering reference leveling component being able to realize superposition of the scanning layer of focus point and the needle-entering layer, as well as to allow the actual needle-entering angle the be just the same as the needle-entering angle requested by the scanning and detecting device with the scanning device gantry being inclined at any angle; as well as the puncturing layer leveling benchmark for perfectly matching the puncturing layer with the scanning layer; therefore, any equivalent variations based on the purposes of the invention shall all belong to the protected scope of the invention. The puncturing guiding method of the invention for the puncturing needle guiding device to perform puncturing under guidance of the scanning device mainly includes: After the patient is removed away from the scanning layer of the scanning devices such as CT and the like, the puncturing needle is guided by utilizing the needle-entering angle guide means of the puncturing needle guiding device, needle-entering layer leveling and guiding components, and scanning layer leveling benchmark to reach the focus point precisely accurately through simple operation; therefore, any equivalent variations based on the purpose shall all belong to the protected scope of the invention.

What is claimed is:

1. A puncturing needle guiding device comprising:
   i) a needle-entering angle guide, adapted to be rotatably connected a needle when placed in said guide via a connector, further including:
      i.a) an angle reference line (N) vertical to a surface where the needle enters, and
      i.b) an indicator of said guide, including a needle-entering angle indicating plate, for indicating an intersected angle between an actual enter direction of the needle and the angle reference line (N),
   ii) a needle-entering layer leveler, sidely affixed to the guide, further comprising
      ii.a) an indicator of said layer leveler, including a scanning layer leveling benchmark, for indicating a deviatingly rotated angle of a rotating plane of the needle, wherein a deviating angle rotating axis of the indicator of said layer leveler is parallel to the guide (W), and
   iii) a reference line leveler, making the angle reference line of the guide (W) on the same plane of a hammer weight line, further comprising:
      iii.a) an indicator of said line leveler, including an angle indicating base plate, wherein
      a deviatingly rotated axis y of the indicator of said line leveler is perpendicular to the deviating angle rotating axis; and
   iv) a level benchmark, making a horizontal line of the rotating plane parallel to a needle-entering layer, and
   v) a top open rectangular casing, including a top opening and is affixed sidely to the guide, with the layer leveler and the line leveler (Y) disposed within, wherein the indicator of the layer leveler and the indicator of the line leveler are exposed in the top opening mounted with a transparent cover.

2. The puncturing needle guiding device as claimed in claim 1, wherein a rotating spindle is at the same axis with the angle rotating axis of the layer leveler;
   said layer leveler and said line leveler being integrally fixed and pivotally installed on said casing with the rotating spindle as a pivotal axis;
   and said rotating spindle includes a protruding extended out of said casing, with an external surface thereof being installed with a rotating angle scale for the rotating spindle, and a knob with a pointer affixed to said protruding.

3. A puncturing guiding method for targeting a focus point by the needle of a puncturing needle guiding device as claimed in claim 1, comprising the following steps:
   1.a) Obtaining 3D coordinates of the focus point by a CT or an MRI scanning device;
   1.b) Obtaining a puncturing sectional layer (Y0Z) from the CT or MRI scanning device,
   1.c) marking on a body skin a needle-entering point, and
   1.d) marking on the body skin a projection line of a scanning layer obtained from the CT or MRI scanning device;
   1.e) calculating a needle-entering angle, based on an angle of a line connecting the point and the needle-entering point relative to a horizontal line, or relative to a vertical line of the horizontal line;
   calculating a needle-entering depth, based on a length of the line;
   2) installing the needle on the needle-entering angle indicating plate of the guide;
   3) Leveling a puncturing needle-entering angle:
   3.a) Adjusting the angle of the needle on the angle scale plate of the guide along an axis of the needle to a scanner-detected angle detected by the CT or MRI scanning device for needle-entering;
   4) Aiming a needle point of the needle at the needle-entering point, allowing the hammer weight line of the line leveler to point at a line of zero degree or zero scale on the angle indicating base plate of the indicator of said line leveler;
   5) Deviatingly rotating the puncturing needle guiding device in accordance with an inclined angle of a CT gantry of the CT or MRI scanning device until reaching the same value of an angle as the angle α displayed by the angle display device of a scanning layer leveling component of the scanning device;
   6) Aiming a scanning layer leveling benchmark of the indicator at the axis of the needle and at the projection line of the scanning layer on the body skin; and
   7) Performing a puncturing according to the needle-entering depth obtained in step 1.e).

4. The puncturing guiding method as claimed in claim 3, wherein the is a bubble level gauge in step 4), a bubble of the bubble level gauge is positioned at the center.

5. The puncturing guiding method as claimed in claim 3, wherein upon the puncturing in step 7) is performed the puncturing is evaluated by a CT scanning.

* * * * *